(12) United States Patent
Konstorum et al.

(10) Patent No.: US 7,852,371 B2
(45) Date of Patent: Dec. 14, 2010

(54) AUTOCLAVABLE VIDEO CAMERA FOR AN ENDOSCOPE

(75) Inventors: Gregory Konstorum, Stamford, CT (US); Tai Lin Fan, Nashua, NH (US); Lawrence St. George, Sudbury, MA (US)

(73) Assignee: Gyrus Acmi, Inc., Southborough, MA (US)

( * ) Notice: Subject to any disclaimer, the term of this patent is extended or adjusted under 35 U.S.C. 154(b) by 1567 days.

(21) Appl. No.: 11/109,902

(22) Filed: Apr. 19, 2005

(65) Prior Publication Data

US 2005/0267329 A1 Dec. 1, 2005

Related U.S. Application Data

(60) Provisional application No. 60/563,857, filed on Apr. 19, 2004.

(51) Int. Cl.
*H04N 7/18* (2006.01)
(52) U.S. Cl. .............................. 348/65; 348/68; 348/75
(58) Field of Classification Search ............... 348/65–76
See application file for complete search history.

(56) References Cited

U.S. PATENT DOCUMENTS

| | | | |
|---|---|---|---|
| 4,389,565 A | 6/1983 | Numata | |
| 4,562,344 A | 12/1985 | Mihara et al. | |
| 4,781,448 A | 11/1988 | Chatenever et al. | |
| 4,905,668 A | 3/1990 | Ohsawa et al. | |
| 5,056,902 A | 10/1991 | Chinnock et al. | |
| 5,122,650 A | 6/1992 | McKinley | |
| 5,191,203 A | 3/1993 | McKinley | |
| 5,212,595 A | 5/1993 | Dennison et al. | |
| 5,359,992 A | 11/1994 | Hori et al. | |

(Continued)

FOREIGN PATENT DOCUMENTS

DE 20104874 8/2001

(Continued)

OTHER PUBLICATIONS

Japanese Office Action dated Feb. 16, 2010 for related Japanese patent application No. 2007-546902; an informal English summary of the Report provided by the Japanese agent is included; 5 pages total.

(Continued)

*Primary Examiner*—Andy S Rao
(74) *Attorney, Agent, or Firm*—Ganz Law, P.C.

(57) ABSTRACT

Sterilizable electronic video cameras for an endoscope are provided. The electronic video camera comprises an enclosure, a lens cell, a lens cell holder, an image sensor, a motorized focusing system, and switch control. The enclosure comprises a housing and a cover, the housing defining a cavity therein. The cover has a window disposed therein, the housing and cover adapted for hermetic coupling. The lens cell is slidably disposed in the lens cell holder. The image sensor is in optical communication with the lens cell and window. The motorized focusing system is adapted to axially reciprocally move the lens cell relative to the lens cell holder controlled by the switch. The switch control is activated external to the enclosure and is hermetically sealed therewith. The lens cell, lens cell holder, image sensor, and the motorized focusing system, as an assembly, are coupled to the cover and disposed within the cavity.

12 Claims, 9 Drawing Sheets

U.S. PATENT DOCUMENTS

| | | |
|---|---|---|
| 5,538,497 A | 7/1996 | Hori |
| 5,582,576 A | 12/1996 | Hori et al. |
| 5,603,687 A | 2/1997 | Hori et al. |
| 5,612,816 A | 3/1997 | Strahle et al. |
| 5,662,584 A | 9/1997 | Hori et al. |
| 5,673,147 A | 9/1997 | McKinley |
| 5,682,199 A | 10/1997 | Lankford |
| 5,850,496 A * | 12/1998 | Bellahsene et al. .......... 385/117 |
| 5,864,359 A | 1/1999 | Kazakevich |
| 5,868,664 A | 2/1999 | Speier et al. |
| 6,030,339 A | 2/2000 | Tatsuno et al. |
| 6,080,101 A | 6/2000 | Tatsuno et al. |
| 6,292,221 B1 | 9/2001 | Lichtman |
| 6,346,073 B1 | 2/2002 | Thompson |
| 6,425,857 B1 | 7/2002 | Rudischhauser et al. |
| 6,464,631 B1 | 10/2002 | Girke et al. |
| 6,500,169 B1 * | 12/2002 | Deng ............................. 606/1 |
| 6,533,721 B1 | 3/2003 | Beutter et al. |
| 6,547,721 B1 | 4/2003 | Higuma et al. |
| 6,572,537 B2 | 6/2003 | Futatsugi et al. |
| 6,716,161 B2 | 4/2004 | Higuma et al. |
| 6,749,561 B2 | 6/2004 | Kazakevich |
| 6,776,328 B2 | 8/2004 | Rice et al. |
| 6,805,664 B2 | 10/2004 | Doyle et al. |
| 7,410,462 B2 | 8/2008 | Navok et al. |
| 2001/0016679 A1 | 8/2001 | Futatsugi |
| 2008/0300463 A1 | 12/2008 | Navok et al. |

FOREIGN PATENT DOCUMENTS

| | | |
|---|---|---|
| GB | 2358312 A | 7/2001 |
| JP | 60-009591 | 1/1985 |
| JP | 61-002834 | 1/1986 |
| JP | 07-047050 | 2/1995 |
| JP | 09-323174 | 12/1997 |
| JP | 10-262927 | 10/1998 |
| JP | 2000-120997 | 4/2000 |
| JP | 2000-287913 | 10/2000 |
| JP | 2001078956 | 3/2001 |
| JP | 2001-212075 | 8/2001 |
| WO | WO2006066022 A2 | 6/2006 |

OTHER PUBLICATIONS

German Examination Report dated Apr. 30, 2010 for related German patent application No. 11205002972.7; an informal English translation of the Report provided by the German agent is included; 8 pages total.

* cited by examiner

AUTOCLAVABLE VIDEO CAMERA FOR AN ENDOSCOPE

This invention claims priority to and the benefit of co-pending U.S. Provisional Application No. 60/563,857 entitled "AUTOCLAVABLE VIDEO CAMERA FOR AN ENDOSCOPE", filed Apr. 19, 2004, the entire disclosure of which is hereby incorporated by reference as if set forth in its entirety for all purposes.

FIELD

The present invention generally relates to medical endoscopes, and more particularly, to sterilizable electronic video cameras for an endoscope.

BACKGROUND

Endoscopes are medical devices which are used to provide external images of organs and structures within a human or animal. As used herein, the term "endoscope" includes, but is not limited to, arthroscopes, colonoscopes, bronchoscopes, hysteroscopes, cystoscopes, sigmoidoscopes, laparoscopes and urethrascopes.

Commonly, endoscopes comprise an insertion portion in the form of a hollow shaft that is designed for insertion through a body orifice or a small incision into an internal body cavity. An objective lens unit consisting of one or more lenses is mounted within the shaft at its distal (forward) end. The objective lens unit forms an image of the area that is viewed by it, i.e., the "target". The image of the target so captured is then transmitted to an optical viewing device or to an electronic imaging device. The hollow shaft may, but need not, include optical image transmission apparatus, e.g., a relay lens, for applying the image to the optical viewing device or to the electronic imaging device.

A conventional optical endoscope provides an optical viewing capability in the form of an eyepiece unit that is affixed to the proximal (rear) end of the shaft. The eyepiece unit is nominally focused to infinity for direct viewing of the image by the surgeon. More specifically, the objective lens unit of a conventional optical endoscope is usually designed so as to form a focused image of an object or other target located at a predetermined target distance therefrom. That predetermined object distance is the object position relative to the objective lens unit which is thought by the designer to be most frequently required by a surgeon. Further, the overall optics system of a conventional optical endoscope is designed so that the image emerging from the eyepiece unit is collimated, i.e., focused nominally to infinity. The cornea of the surgeon's eye acts to focus the collimated image beam on the retina of the surgeon's eye during direct viewing of the image by the surgeon.

Another type of endoscope is an integrated video endoscope that incorporates a video camera. As used herein, the term "video camera" is used to designate a solid state, electronic imaging device, such as, but not limited to, a charge coupled device ("CCD") and complementary metal oxide semiconductor (CMOS) imaging devices. In some integrated video endoscopes, the solid state imaging device is mounted within the hollow endoscope shaft, or in a housing that is attached to the proximal end of the shaft. The electronic imaging device generates electrical signals representative of the images received from the objective lens unit. Those signals are then processed to generate video signals which are used to create a video display on a conventional TV monitor or a head-mounted video display unit, for example. In this connection, it should be noted that in addition to the electronic imaging device, the camera may comprise one or more circuits for controlling the operation of the electronic imaging device and processing the electronic imaging device's output signals.

A conventional optical endoscope may be converted to a video endoscope by attaching a video camera to the endoscope in a position to receive the image passed by the eyepiece unit (as used herein the term "video camera" designates a housing that contains a video camera and that is adapted to be connected to an endoscope directly or via an endoscope coupler). The video camera may be used with many different endoscopes, thereby providing significant cost savings over the alternative of providing an integrated video endoscope for each type of surgical procedure. However, since the exit image of the conventional eyepiece unit is generally collimated, and since the target distance will vary as the endoscope is manipulated by the surgeon, it is desirable to provide a focusing device between the video camera and the conventional optical endoscope so that the image passed by the eyepiece unit can be focused so as to accommodate a wide range of object distances. The use of such a focusing device has the effect of changing the magnification, and hence the field of view, of the image, while keeping the image properly focused on the camera image plane.

Known focusing couplers include a focusing lens cell mounted for reciprocal movement within a coupler housing, and a manually movable actuating means located outside of the housing which is mechanically or magnetically coupled to the focusing lens cell for moving the cell so as to focus the image on the image plane of the electronic imaging device of a video camera.

All such externally operable focusing couplers provided for use with conventional optical endoscopes are characterized by several disadvantages. For example, to the extent that such focusing couplers involve externally movable elements having close fitting surfaces, such as manually rotatable focusing rings, the areas between the closely fitting surfaces provide areas into which micro-organisms can enter. These small areas present sterilization issues.

Activation of a focusing system for the lens cell is particularly difficult with steam-sterilizable electronic video endoscopes as the sealed housing precludes direct contact with the focusing system. A known method of focus control includes a rotatable collar that contains permanent magnets that magnetically couple with complementary permanent magnets on the focusing system within the housing. Through magnetic coupling, the user can move the lens cell with respect to the image sensor by rotating the external focusing ring. Since there is no breach of the housing by the magnetic coupling, the hermetic seal is maintained. However, the foregoing system has disadvantages. For example, the magnetic coupling system is bulky, focus precision can be difficult to maintain, and the focusing ring presents sterilization issues.

Steam-sterilizable electronic video endoscopes are known in which an image sensor and lens cell are housed in a hermetically-sealed housing using O-rings, which are adversely affected by repeated heat or steam sterilization. The O-rings fail over time breaching the hermetic seal.

What is needed in the art is a video camera for an endoscope that is hermetically sealed and allows for steam sterilization while incorporating a reliable focusing mechanism.

SUMMARY

An embodiment of an electronic video camera for an endoscope, comprising an enclosure, a lens cell, a lens cell holder, an image sensor, a motorized focusing system, and switch control. The enclosure comprises a housing and a cover, the housing defining a cavity therein. The cover has a window disposed therein, the housing and cover adapted for hermetic coupling. The lens cell has at least one lens, the lens cell being slidably disposed in the lens cell holder. The image sensor is in optical communication with the lens cell and window. The motorized focusing system is adapted to axially reciprocally move the lens cell relative to the lens cell holder controlled by the switch control. The switch control is activated external to the enclosure and is hermetically sealed therewith. The lens cell, lens cell holder, image sensor, and the motorized focusing system, as an assembly, are coupled to the cover and disposed within the cavity.

The cavity is defined by a single axial bore, wherein the lens cell holder, the lens cell, the image sensor, and the motorized focusing system are adapted to be disposed within the axial bore.

The housing has a housing proximal end that is closed and a housing distal end that is open. The cover has a cover interior side and a cover external side. The cover external side defines a stepped annular aperture. The window is hermetically sealed within the stepped annular aperture. The window is adapted to be optically transparent. The cover exterior side is adapted to optically and mechanically couple with an endoscope.

The housing proximal end comprises a cable connector hermetically coupled with the housing and adapted to allow electrical communication therethrough. In the cavity adjacent to the housing proximal end are electronic connectors in electrical communication with the cable connector, wherein the motorized focusing system and the image sensor are in electrical communication with the electronic connectors.

The motorized focusing system comprises a motor and associated drive components. The motor is coupled to the lens cell holder and adapted to linearly translate the lens cell within the lens cell holder.

In an embodiment, the associated drive components comprise a pinion gear disposed on a motor drive shaft extending from the motor. The lens cell comprises a gear rack having of a series of rack teeth that are adapted to be cooperatively engaged by the pinion gear. The rack teeth are adapted to mesh closely with the gear teeth so that rotation of the pinion gear will cause the lens cell to move longitudinally in the lens cell holder, in axial alignment with the optical axis, with a minimum of hysteresis or backlash.

In another embodiment, the lens cell further comprises a key depending therefrom, and the lens cell holder further comprises a keyway. The key is adapted to cooperate with the keyway for the retention of rotational alignment of the lens cell relative to the lens cell holder and to limit the range of linear travel there between.

The switch control comprises a keypad having a button and a sensor switch for opening and closing an electrical circuit, the keypad adapted to retain a steam-sterilizable hermetic seal between the button and the sensor switch.

In an embodiment, the keypad comprises an optical coupling between the button and the sensor switch.

In another embodiment, the keypad comprises magnetic coupling between the button and the sensor switch.

In another embodiment, the keypad comprises mechanical coupling between the button and the sensor switch.

An embodiment of a keypad for maintaining a hermetic seal with a housing comprises a means for sensing finger motion and a means for converting that motion to an electric signal transmitted internal to the housing. The keypad comprises a plurality of switch sensors coupled to the housing, the sensors covered with a barrier that is hermetically sealed with the housing.

In another embodiment of a keypad for maintaining a hermetic seal with a housing, the switch sensors comprise a multiple dome keypad (MDK) and keypad electrical connectors. The MDK comprises a plurality of flexible membrane elements that are pressure sensitive and respond to finger pressure to close an electrical switch. The MDK is coupled on the housing and hermetically sealed therewith with a flexible membrane barrier. The flexible membrane barrier is adapted to allow finger pressure to deform the flexible membrane barrier so as to allow contact with snap buttons. The electrical connectors are adapted to be coupled to associated electronics controlling the motorized focusing system and image sensor.

The housing comprises a housing aperture adapted to accept the keypad. The aperture has a first step, a second step, and a third step, of decreasing dimensions. The keypad comprises a plurality of switch sensors mounted into a sensor bezel, the sensor bezel comprising a peripheral edge adapted to couple with the third step. The keypad further comprises a barrier adapted to provide a hermetic seal with the second step covering the sensors. The keypad further comprising a flexible membrane adapted to couple with the first step and provide an attachment for a plurality of targets disposed in cooperative alignment with the sensors. The flexible membrane further comprises a raised edge disposed about the periphery of the flexible membrane adapted to provide an edge seal. The keypad further comprises an outer bezel adapted to be disposed over the flexible membrane in sealing engagement therewith, and coupled to the housing. The outer bezel is adapted to compress the raised edge of the flexible membrane for fluid tight engagement therewith, the outer bezel is provided with an aperture associated with each of the targets.

In an embodiment of the keypad, the sensor is an optical reflective sensor-switch which responds to an optical input, the barrier is a transparent material, and the target is a reflective material, wherein finger pressure on the flexible membrane changes the position of the target which results in a change in the optical coupling between the target and the sensor. The sensor responds to the change in optical coupling by closing or opening an electrical connection.

In another embodiment of the keypad, the sensor is a magnetic-flux responsive switch which responds to a change in magnetic flux. The barrier is a non-magnetic-material, and the target is a magnet. Wherein pressure on the flexible membrane changes the position of the magnet which results in a change in the magnetic flux on the sensor. The sensor responds to the change in magnetic flux by closing or opening an electrical connection.

In another embodiment of the keypad, the sensor is a capacitive sensor circuit which responds to a change of capacitance. The barrier is a polymeric material that is non-conductive. The target is an electrically-conductive metal adapted to sense changes in capacitance at the capacitive sensor circuit. The capacitive sensor circuit responds to the change in capacitance by closing or opening an electrical connection.

In another embodiment of the keypad, the sensor is a pressure sensitive sensor which responds to pressure. The barrier is a thin sheet adapted to flex under pressure. The target is a push button, wherein pressure deforms the thin sheet to allow pressure onto the pressure sensitive sensor. Wherein the sensor responds to the change in pressure by closing or opening an electrical connection.

DETAILED DESCRIPTION

Figure 1:
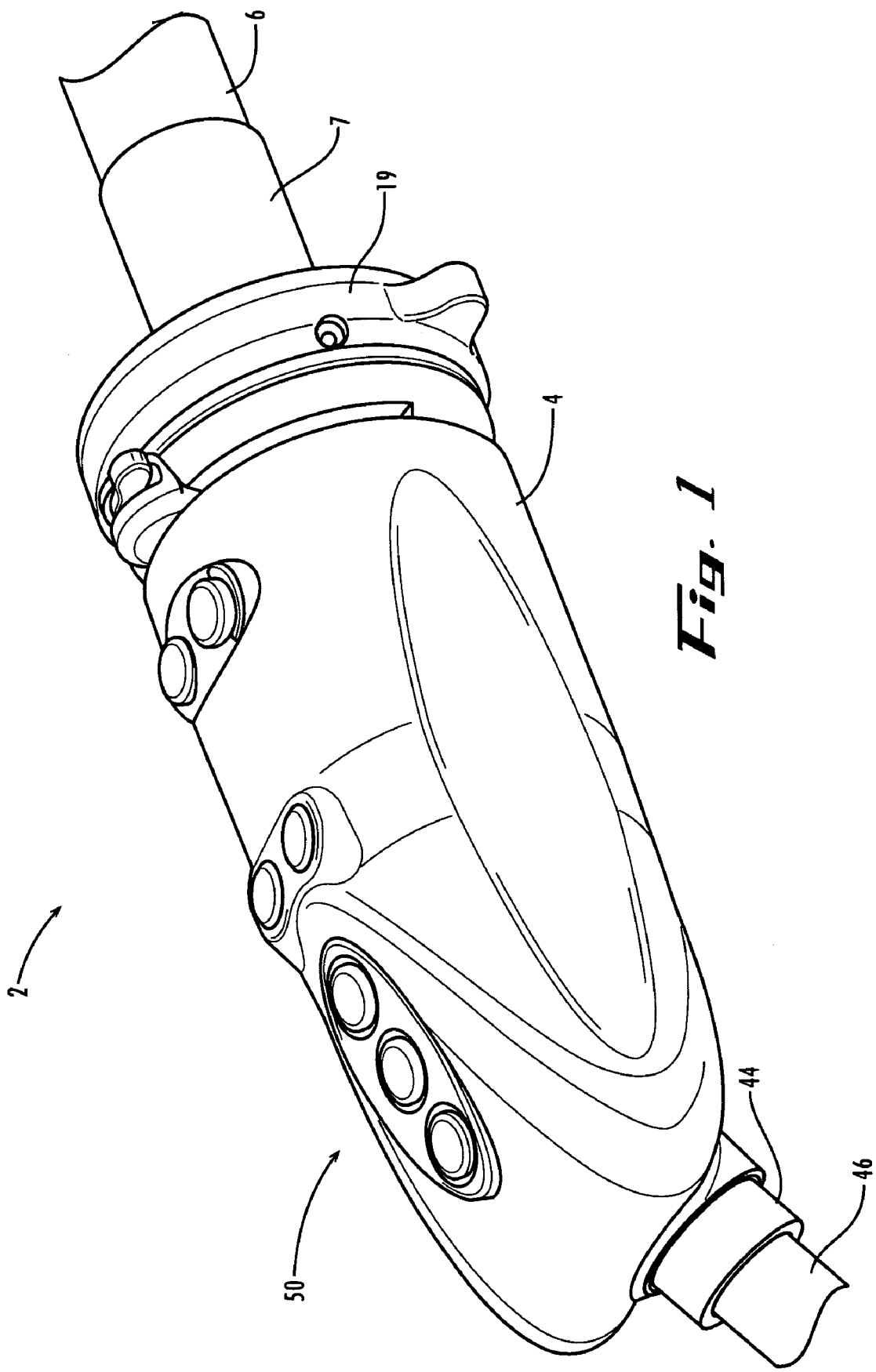
FIG. 1 is a perspective view of an endoscope system comprising a video camera and an endoscope in accordance with an embodiment of the present invention.

A steam sterilizable electronic video camera for an endoscope is provided in which an image sensor, lens cell and motorized focusing system is housed in a hermetically sealed housing, which is not adversely affected by heat or steam sterilization. Similarly, the associated electronics is arranged in the housing and is formed of heat resistant material. Activation of an electric motor of the focusing system is via a keypad on the housing that transmits the commands of the operator while retaining a hermetic seal that is capable of withstanding repeated autoclave sterilizations.

FIGS. 1-5 are perspective and cross-sectional views, respectively, of an endoscope video camera 4, in accordance with embodiments of the present invention. The endoscope video camera 4 is adapted for coupling into an optical path extending from a conventional optical endoscope 6, as discussed hereinafter in greater detail.

The endoscope video camera 4 comprises an enclosure 10, a lens cell 20, an image sensor 40, associated electronics 42, motorized focusing system 30, switch control 54, a cover 15, and a cable connector 44. The enclosure 10 comprises a housing 11 and the cover 15. The housing 11 comprises a deep cavity 12 having a housing proximal end 13 that is closed and a housing distal end 14 that is open. The cavity 12 is adapted to contain the lens cell 20, lens cell holder 21, image sensor 40, associated electronics 42, and the motorized focusing system 30. The housing distal end 14 is adapted to couple with the cover 15 and to hermetically seal the lens cell 20, lens cell holder 21, image sensor 40, associated electronics 42, and the motorized focusing system 30 within the cavity 12.

The cover 15 has a cover interior side 16 and a cover external side 17. The cover 15 has a widow aperture 18 in the form of a stepped annular aperture in which is positioned a window 27 of transparent material. The window 27 can be any transparent material suitable for a particular purpose, such as, but not limited to, glass and sapphire. In an embodiment in accordance with the present invention, the window 27 comprises sapphire with a metalized perimeter for hermetically coupling the window 27 to the widow aperture 18, using techniques such as, but not limited to, soldering and welding, to make a hermetic seal with the cover 15. In other embodiments, the window 27 is secured in place by a cement so as to make a hermetic seal with the cover 15. The window 27 or an element of the lens set 23 may also comprise an infrared (IR) filter.

Figure 2:
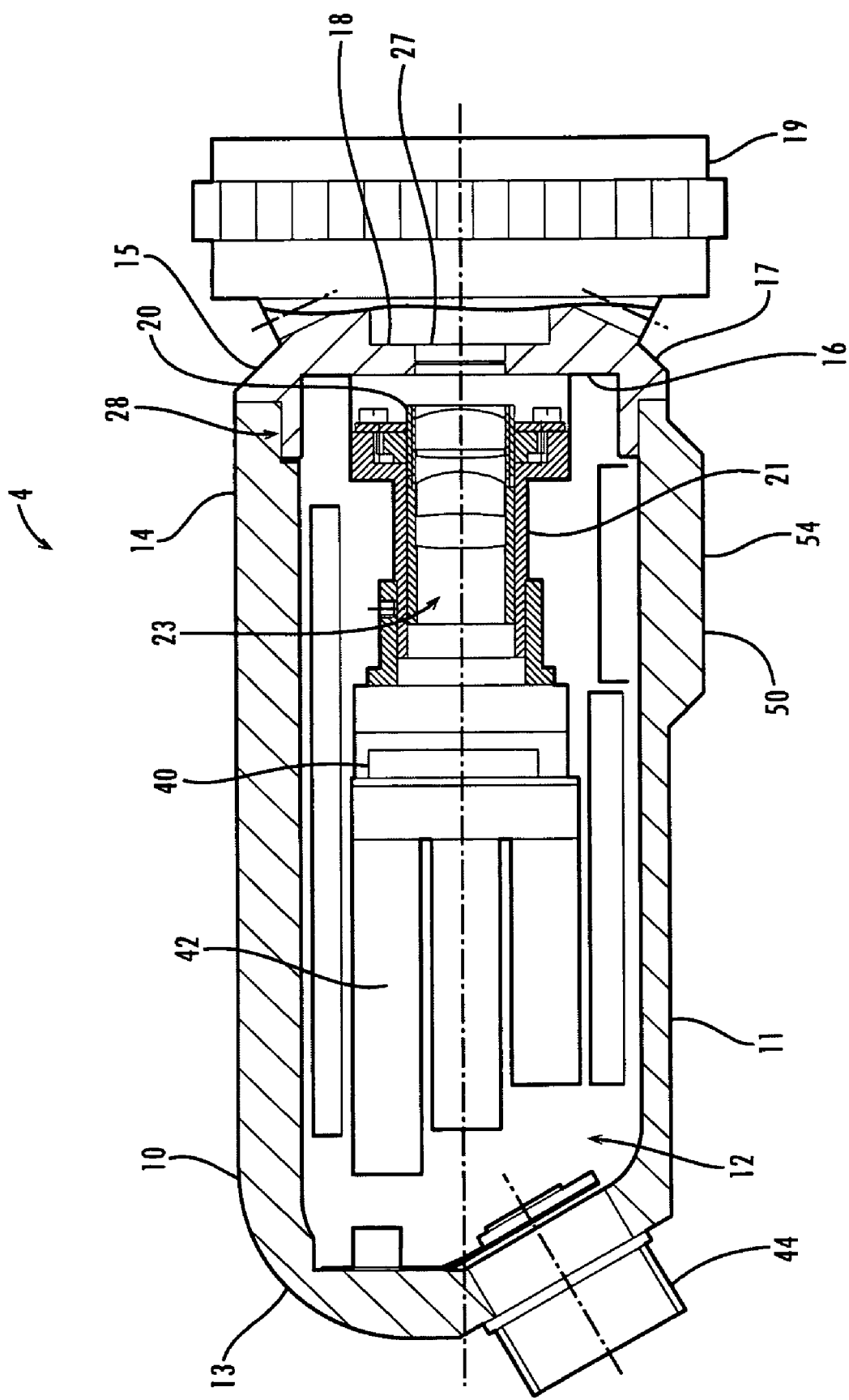
FIG. 2 is a side cross-sectional view of a video camera, in accordance with an embodiment of the present invention.
Figure 3:
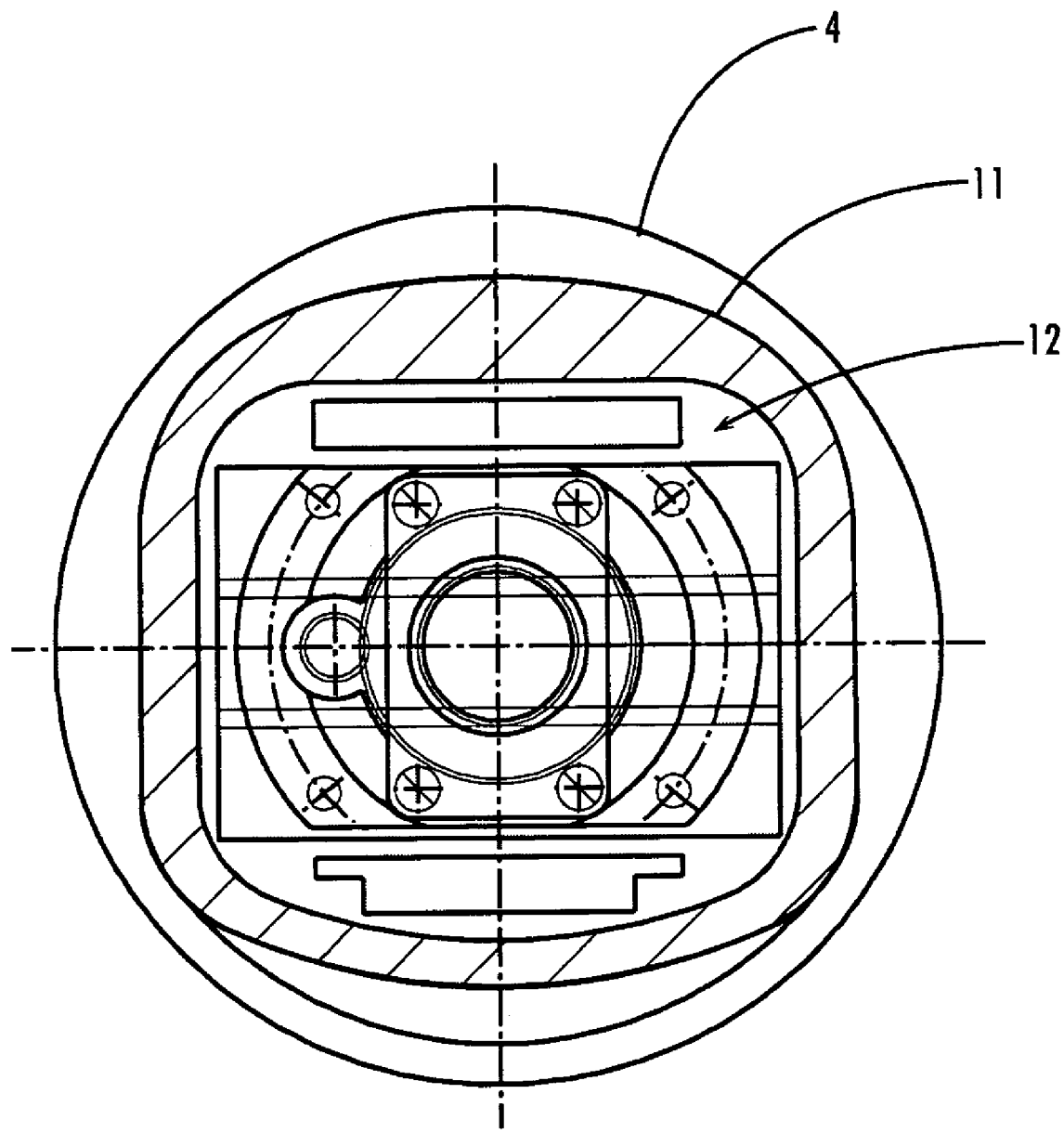
FIG. 3 is an end cross-sectional view of the embodiment of FIG. 2.
Figure 4:
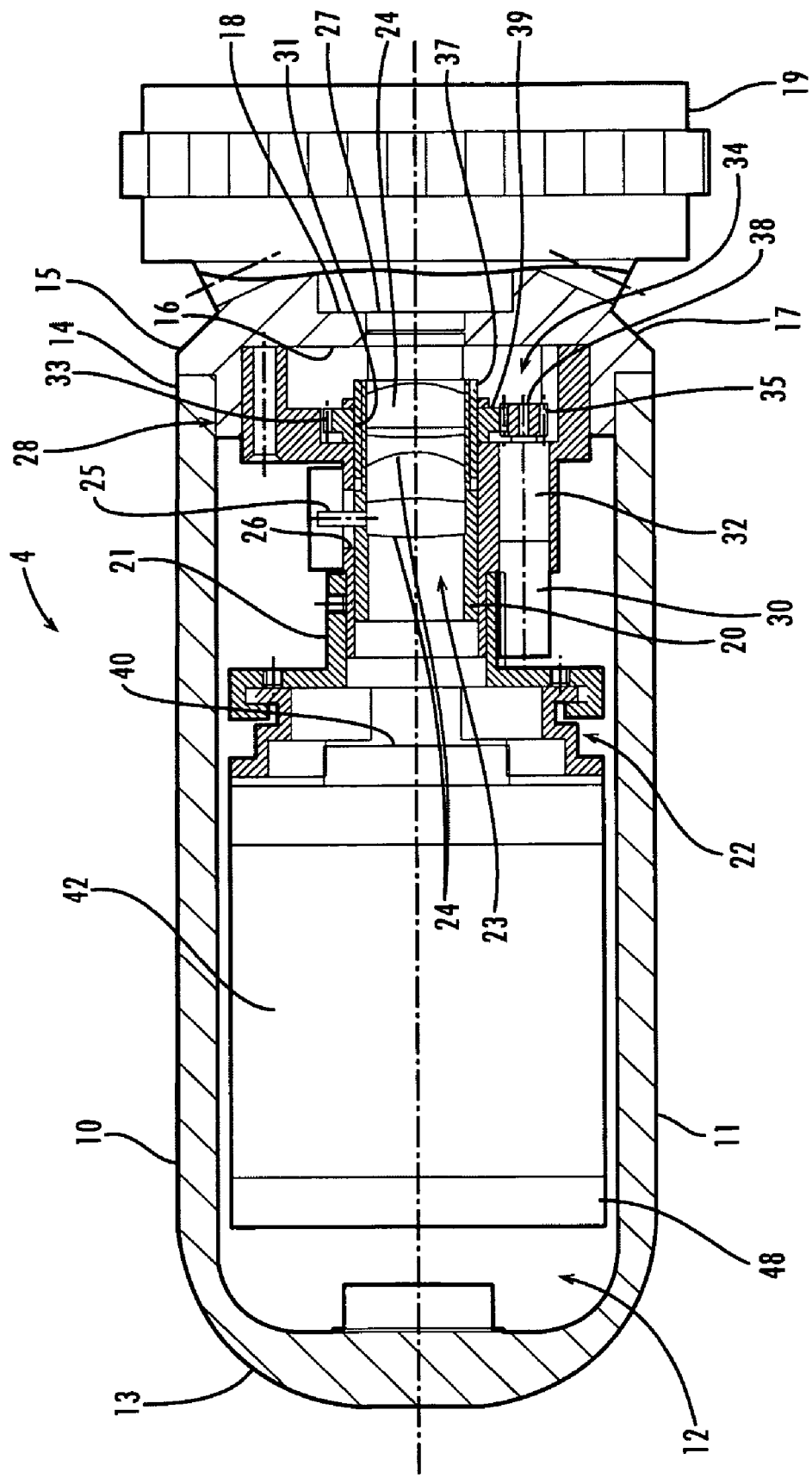
FIG. 4 is a top cross-sectional view of the embodiment of FIG. 2.

The cover exterior side 17 is also adapted to optically and mechanically couple with an endoscope 6. Referring to FIGS. 1, 2 and 4, the cover exterior side 17 is provided with a coupler 19 which is adapted to releasably couple with an eyepiece 7 of an optical endoscope 6. When the coupler 19 is coupled with the endoscope 6, the center axes of the lens cell 20 and image sensor 40 are aligned with the optical axis of the endoscope 6 through the window 27.

The cover 15 is adapted to be hermetically sealed with the housing distal end 14. In the embodiment of FIG. 2, a stepped joint 28 between the periphery of the cover 15 and the housing distal end 14 is provided that is adapted to be coupled using techniques such as, but not limited to, soldering and welding, to make a hermetic seal.

The cover interior side 16 is adapted to couple with an assembly comprising the lens cell holder 21, the lens cell 20, the image sensor 40, the associated electronics 42, and the motorized focusing system 30. This is advantageous in that the optical path of the window 27, the lens cell 20 and the image sensor 40 can be aligned and verified prior to assembly into the housing 11. Also, the operation of the motorized focusing system 30 can be verified prior to assembly into the housing 11. Further, the operation of the image sensor 40 can be verified prior to assembly into the housing 11.

The lens cell 20, the lens cell holder 21, the image sensor 40, the associated electronics 42, and the motorized focusing system 30 are coupled as a unit and inserted as a unit into the cavity 12 when the cover 15 is coupled to the housing 11. This combination of features is also advantageous in that it facilitates removal of the lens cell holder 21, the lens cell 20, the image sensor 40, the associated electronics 42, and the motorized focusing system 30 from the housing 11 upon removal of the cover 15.

In an embodiment, the image sensor 40 is coupled to the lens cell holder 21 by a lens cell coupler 22. The lens cell coupler 22 provides an "insert, push in, and 90 degree turn" connection to couple together and ensure alignment of the optical system 30, as shown in FIG. 4.

The proximal end of the housing 11 comprises a cable connector 44 adapted to provide a coupling and hermetically-sealed electrical pass-through from the cavity 12 to an electrical cable 46 (shown in FIG. 1). The cable 46 contains conductors for operating the image sensor 40 and recovering output signals from the image sensor 40, plus conductors connected to wiring for powering the motor 32 of the motorized focusing system 30.

The cavity 12 adjacent to the housing proximal end 13 comprises electronic connectors 48, such as, but not limited to, printed circuit board edge connector sockets, that are in electrical communication with the cable connector 44. The electronic connectors 48 are adapted to electrically couple with complementary connectors, such as, but not limited to, printed circuit board edge connectors, associated with the associated electronics 42 of the image sensor 40 and the motorized focusing system 30.

The image sensor 40 is a solid state imaging device. Such solid state imaging devices include, but are not limited to, charged coupled devices (CCD) and complementary metal oxide semiconductor (CMOS) imaging devices, illustrated schematically in FIGS. 2 and 4. The image sensor 40 generates electrical signals representative of the images received from the lens cell 20. Those signals then are processed to generate video signals which are used to create a video display, such as on a conventional TV monitor or a head-mounted video display unit, for example. In this connection, it should be noted that in addition to the image sensor 40, the video camera 4 may comprise one or more circuits for controlling the operation of the image sensor 40 and processing the image sensor's 40 output signals.

The lens cell 20 is adapted to be slidably disposed in the lens cell holder 21. The distance that the lens cell can translate within the lens cell holder 21 is defined as the lens cell 20 travel. The lens cell 20 is generally a hollow cylinder that comprises a lens set 23 that is disposed in and fixed to the lens cell 20. In the embodiment shown in FIGS. 2 and 4, the lens set 23 comprises three lenses 24 having their optical axes aligned therewith. It should be noted that the number, configurations and spacing of the lenses 24 in the lens set 23 is not critical to the invention. The lenses 24 are adapted to sharply focus the optical image passed by the endoscope onto the image plane of the image sensor 40, which will be described below.

If a conventional optical endoscope 6 is coupled to the coupler 19 of an endoscope video camera 4 as described above, and if then the endoscope 6 is positioned at its nominal (designed) object distance, the image passing out of the proximal (rear) end of the endoscope 6 will be collimated, in which case the lenses 24 serve to focus the image onto the image plane of the image sensor 40 contained within the cavity 12 and aligned with the optical path of the lens cell 20. The lenses 24 may be designed so that a collimated beam (i.e., focused substantially to infinity) from the endoscope 6 is sharply focused on the image sensor 40 when the lens cell 20 is approximately equidistant from the opposite ends of the lens cell travel. If the endoscope 6 is disposed at some other object distance, then the image passed by the endoscope 6 will either converge or diverge according to the particular object distance. Lenses 24 are shaped to focus the image passed by the endoscope 6 onto the image plane of the image sensor 40 over a wide range of object distances. Since magnification and fields of view (which are related inversely to each other) are dependent upon the object distance, the video camera 4 provides a sharply focused image over a wide range of magnifications and fields of view resulting from changes in object distance.

The lens cell 20 further comprises a key 25 adapted to cooperate with a keyway 26 in the lens cell holder 21, or vice versa, for the retention of rotational alignment of the lens cell 20 relative to the lens cell holder 21 and to limit the range of linear travel. In the embodiment of FIGS. 2-5, the lens cell 20 comprises a key 25 in the form of a guide pin extending laterally to the axis of the lens cell 20. The lens cell holder 21 comprises a keyway 26 in the form of a guide pin slot extending longitudinally to the axis of the lens cell holder 21. The key 25 is adapted to slidably engage the keyway 26. The keyway 26 is adapted to control the extreme limits of linear travel of the lens cell 20 within the lens cell holder 21. In addition, the keyway 26 is adapted to control the rotational alignment of the lens cell 20 with the lens cell holder 21. In other embodiments in accordance with the present invention, the key 25 is adapted to cooperate with electrical switches (not shown) adapted to provide electrical signals, such as but not limited to, to trigger a position indicator and to control the motorized focusing system 30 to stop further advancement of the lens cell 20 beyond a predetermined extreme of linear advancement.

The motorized focusing system 30 comprises a motor 32 and associated drive components 34, such as gears and the like. The motor 32 is coupled to the lens cell holder 21. In an embodiment, the motor 32 is provided with a pinion gear 38 disposed on a motor drive shaft (not shown). The position, diameter, and the teeth of the pinion gear 38 are adapted so that the gear teeth mesh with external threads, a lens cell gear 39 and the like, disposed on the lens cell 20.

In the embodiment of FIG. 4, the associated drive components 34 comprise lens cell external threads 37, a lens cell gear 39, and a pinion gear 38. The outer surface of the lens cell 20 is provided with lens cell external threads 37. A lens cell gear 39 comprises lens cell gear internal threads 31 and lens cell gear external teeth 33. The lens cell gear internal threads 31 are adapted to mesh closely with the lens cell external threads 37. The lens cell gear external teeth 33 are adapted to mesh closely with pinion gear teeth 35.

In operation, the motor 30 drives the pinion gear 38, which drives the lens cell gear 39, which, in turn, causes the lens cell 20 to move longitudinally in the lens cell holder 21, in axial alignment with the optical axis, with a minimum of hysteresis or backlash. The pinion gear 38 and the lens cell gear 39 are restrained from moving longitudinally, and therefore, the lens cell 20 is caused to move longitudinally by the cooperative engagement of the lens cell gear internal threads 31 and the lens cell external threads 37. The cooperative engagement of the key 25 in the keyway 26 prevents rotation of the lens cell 20 relative to the lens cell holder 21 while allowing it to move longitudinally in the lens cell holder 21. The lens cell 20 can be selectively moved in the lens cell holder 21 in a proximal or distal direction, relative to the image sensor 40, by operation of the motor 32.

It is understood that many drive component arrangements may be utilized to effectively replace the pinion gear 38 and the lens cell gear 39 combination, and is not limited thereto. In another embodiment in accordance with the present invention, a worm gear is coupled to the drive shaft of the motor 32 and put in cooperative engagement with the lens cell external threads 37 on the lens cell 20. It is understood that since the motor drive components 34 may be assembled when the motor drive components 34 are not disposed within the housing 11, assembly is made easier and facilitates a greater choice of gear components. By way of example, wherein a worm gear is disposed on the motor drive shaft, the worm gear may be brought into engagement with the lens cell gear 39 on the lens cell 20 from a lateral direction. And wherein a pinion gear 38 is disposed on the motor drive shaft, the pinion gear 38 may be brought into engagement with the lens cell gear 39 on the lens cell 20 from a longitudinal direction.

The motor 32 may be an a.c. or d.c. motor. The motor 32 is coupled to the lens cell holder 21 by a plurality of screws (not shown) that are screwed into threaded holes (not shown) in the lens cell holder 21. Other means may be used to couple the motor 32 to the lens cell holder 21. Electric terminals (not shown) of the motor 32 are connected to a power source (not shown) and controlled via the switch control 54 comprising a keypad 50.

The keypad 50 is adapted to activate the motor 32 and also cause it to selectively operate the lens cell 20 in a forward or reverse direction. In an embodiment in accordance with the present invention, two switches are provided in the keypad 50. The switches are connected to the power circuit for the motor 32, with a first switch when closed serving to energize the motor 32 in a forward direction, and a second switch when closed serving to energize the motor 32 in the reverse direction. Additional switch means may be incorporated into housing 11 for the purpose of providing manual control of the camera operating circuits. Specific embodiments of switches are further described below.

As noted above, the motor 32 may be operated to rotate the pinion gear 38 in either a clockwise or a counterclockwise direction, causing the lens cell 20 to move proximally toward the image sensor 40 or distally away from the image sensor 40. It has been found that a motor speed/gearing ratio arrangement which results in a longitudinal movement of the lens cell 20 relative to the lens cell holder 21 of about 12 mm in about 3 seconds is satisfactory.

Figure 6:
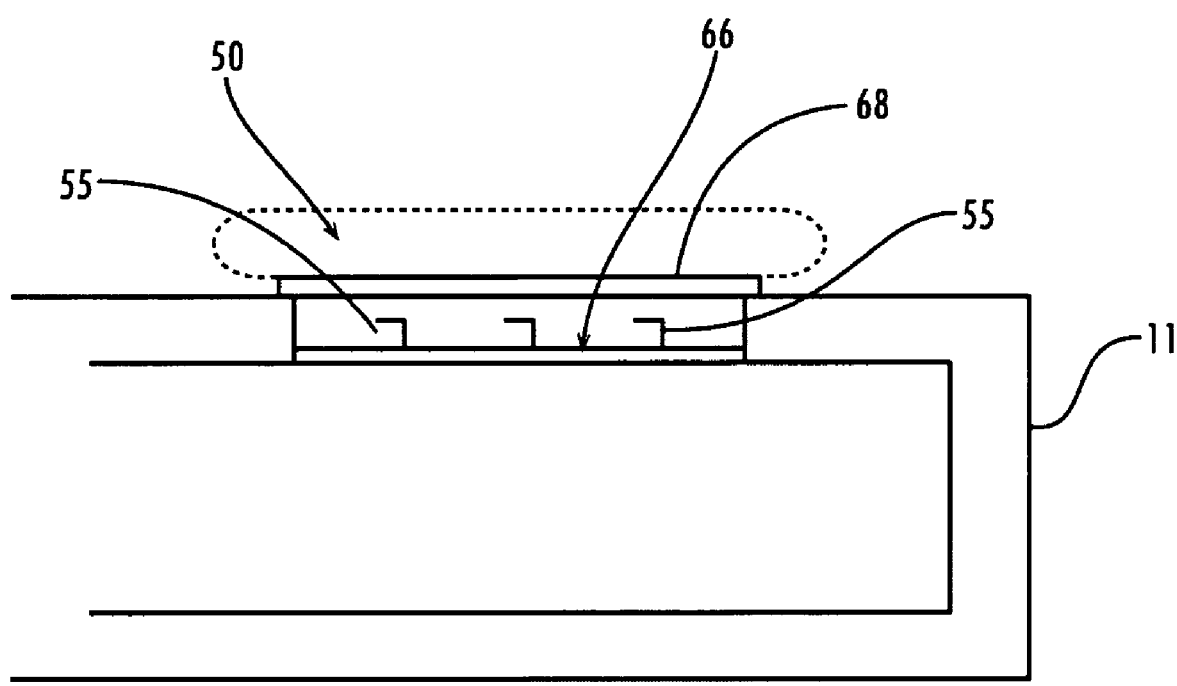
FIG. 6 is a cross-sectional view of a hermetically sealed keypad, in accordance with an embodiment of the present invention.

FIG. 6 is a cross-sectional view of a keypad 50 which maintains a hermetic seal with the housing 11, in accordance with an embodiment of the present invention. The keypad 50 comprises a means for sensing finger motion and a means for converting that motion to an electric signal transmitted internal to the housing 11.

In the embodiment of FIG. 6, the keypad 50 comprises a plurality of switch sensors 55 coupled to the housing 11, the switch sensors 55 are covered with a barrier 68 that is hermetically sealed with the housing 11. The switch sensors 55 detect finger motion by any suitable means, such as, but not limited to, mechanical, electrical, chemical and optical means. The switch sensors 55 detect the motion of the operator's finger(s) and responds in a predetermined manner to control the electronics associated with the image sensor 40 and the motorized focusing system 30.

In an embodiment in accordance with the present invention, the switch sensors comprise a multiple dome keypad (MDK) and keypad electrical connectors. The MDK comprises a plurality of flexible membrane elements, such as, but not limited to, snap buttons or bubbles, that are pressure sensitive and respond to finger pressure to close an electrical switch. The MDK is mounted on the housing and hermetically sealed therewith with a flexible membrane barrier. The flexible membrane barrier is adapted to allow finger pressure to deform the flexible membrane barrier so as to allow contact with the snap buttons. The electrical connectors are coupled with the associated electronics controlling the motorized focusing system and image sensor.

Other embodiments for providing motion coupling or detection include: optical coupling; magnetic coupling; capacitive coupling; pressure coupling; among others. Essentially, any mechanical, electrical, optical, and even chemical means that are capable of differentiating the states of different buttons (switches) to detect one or a combination of keys that are meant to be activated will be qualified as a motion finger detecting means, and be used to activate the switches.

Both optical sensor/switches and Hall-effect sensor/switches are active components that will need to be powered, and thus take electric current to be alive. Reed magnetic sensor/switches do not need to be powered, and therefore, do not divert electric current from the power source.

Figure 7:
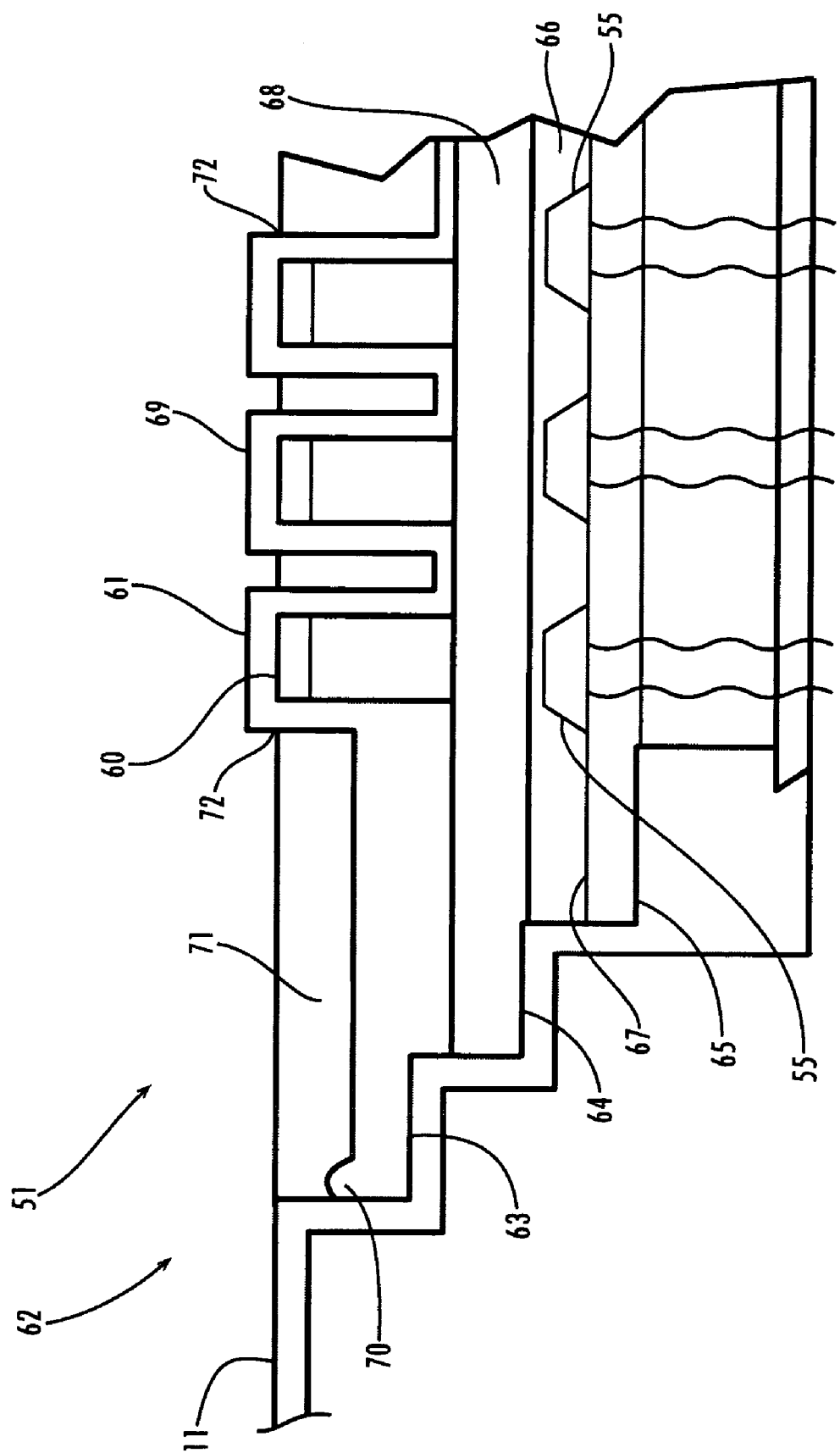
FIG. 7 is a cross-sectional view of a keypad, in accordance with another embodiment of the present invention.

FIG. 7 is a cross-sectional view of a keypad 51 which maintains a hermetic seal with the housing 11, in accordance with another embodiment of the present invention. Switching is accomplished by a finger touch/push of a sensor target 60, with the switch sensor 55 sensing the sensor target 60 by various means across the hermetic barrier 61 to detect the mode of triggering the switch sensor 55, including, but not limited to, approaching towards, moving away, hovering, and lateral motion of the sensor target 60. The hermetic barrier 61 can be in the form of a membrane, plate, thin wall, glass, or other suitable material for a particular purpose.

A housing aperture 62 is provided in the housing 11 to accept the keypad 51 as shown in FIG. 7. The aperture 62 provides a series of three steps, a first step 63, a second step 64, and a third step 65, of decreasing dimensions, so as to accept the peripheral edges of various components described below.

The keypad 51 comprises a plurality of switch sensors 55 mounted into a sensor bezel 66. The sensor bezel 66 comprises a peripheral edge 67 adapted to couple with the third step 65. The keypad 51 further comprises a barrier 68 adapted to provide a hermetic seal with the second step 64 covering the switch sensor 55. The keypad 51 further comprises a flexible membrane 69 adapted to couple with the first step 63 and provide an attachment for a plurality of sensor targets 60 disposed in cooperative alignment with the switch sensor 55. The flexible membrane 69 further comprises a raised edge 70 disposed about the periphery of the flexible membrane 69 adapted to provide an edge seal. The keypad 51 further comprises an outer bezel 71 adapted to be disposed over the flexible membrane 69 in sealing engagement therewith, and coupled to the housing 11 using techniques such as, but not limited to, soldering and welding, to make a hermetic seal. The outer bezel 71 is adapted to compress the raised edge 70 of the flexible membrane 69 for fluid tight engagement therewith. The outer bezel 71 is provided with an outer bezel aperture 72 associated with each of the sensor targets 60.

Figure 8:
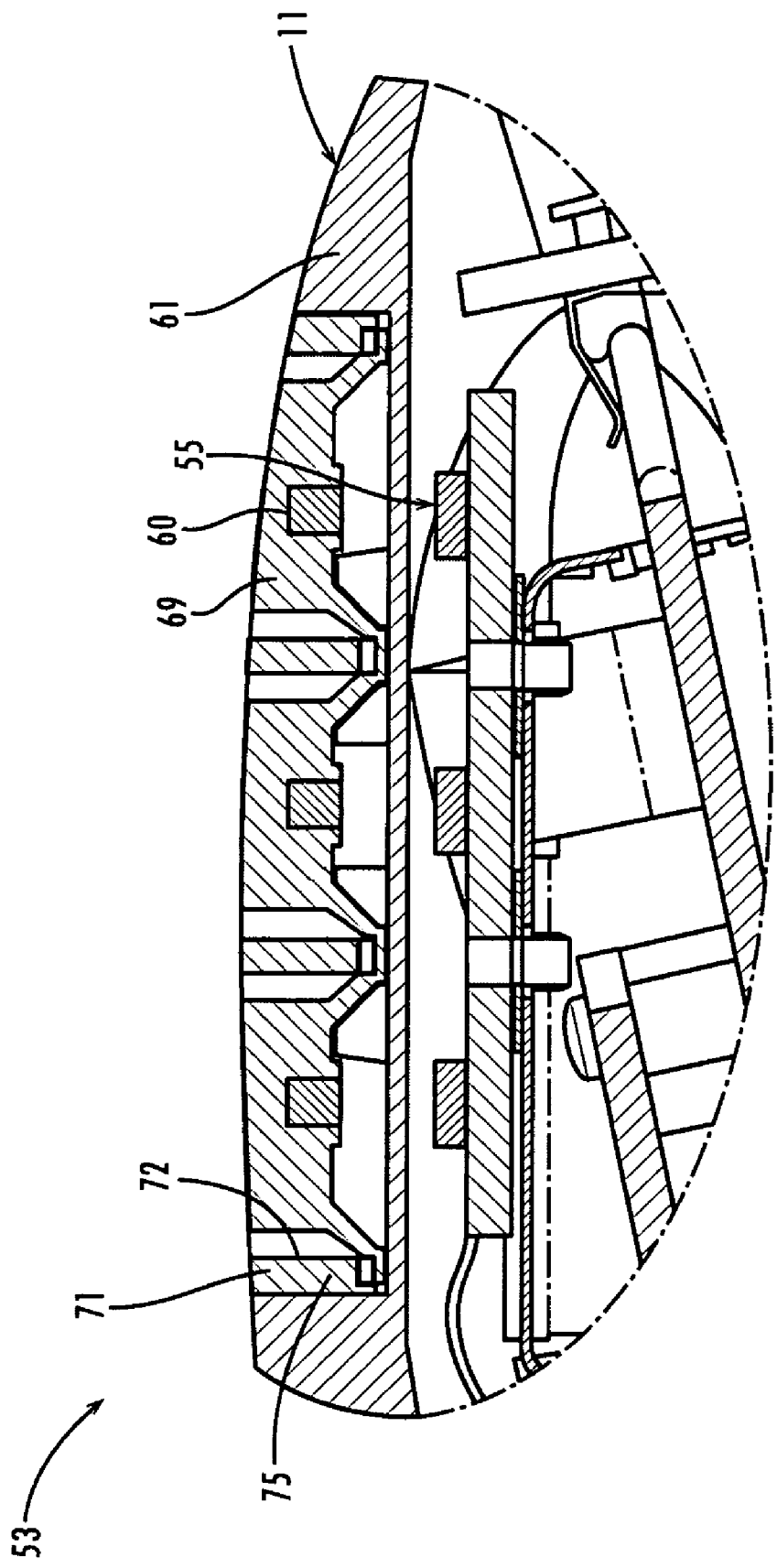
FIG. 8 is a cross-sectional view of a keypad, in accordance with another embodiment of the present invention.

FIG. 8 is a cross-sectional view of a keypad 53 which maintains a hermetic seal with the housing 11, in accordance with another embodiment of the present invention. Switching is accomplished by a finger touch/push of a sensor target 60, with the switch sensor 55 sensing the sensor target 60 by various means across the hermetic barrier 61; The hermetic barrier 61 is an integral part of the housing 11, such as, but not limited to, a recessed portion, defining a keypad socket 75, in the housing 11, wherein the housing 11 comprises a material that allows communication between the sensor target 60 external to the housing 11 and the switch sensor 55 that is internal to the housing 11. In other embodiments in accordance with the present invention, the hermetic barrier 61 can be in the form of a membrane, plate, thin wall, glass, or other material suitable for a particular purpose, hermetically sealed with the housing 11.

Figure 5:
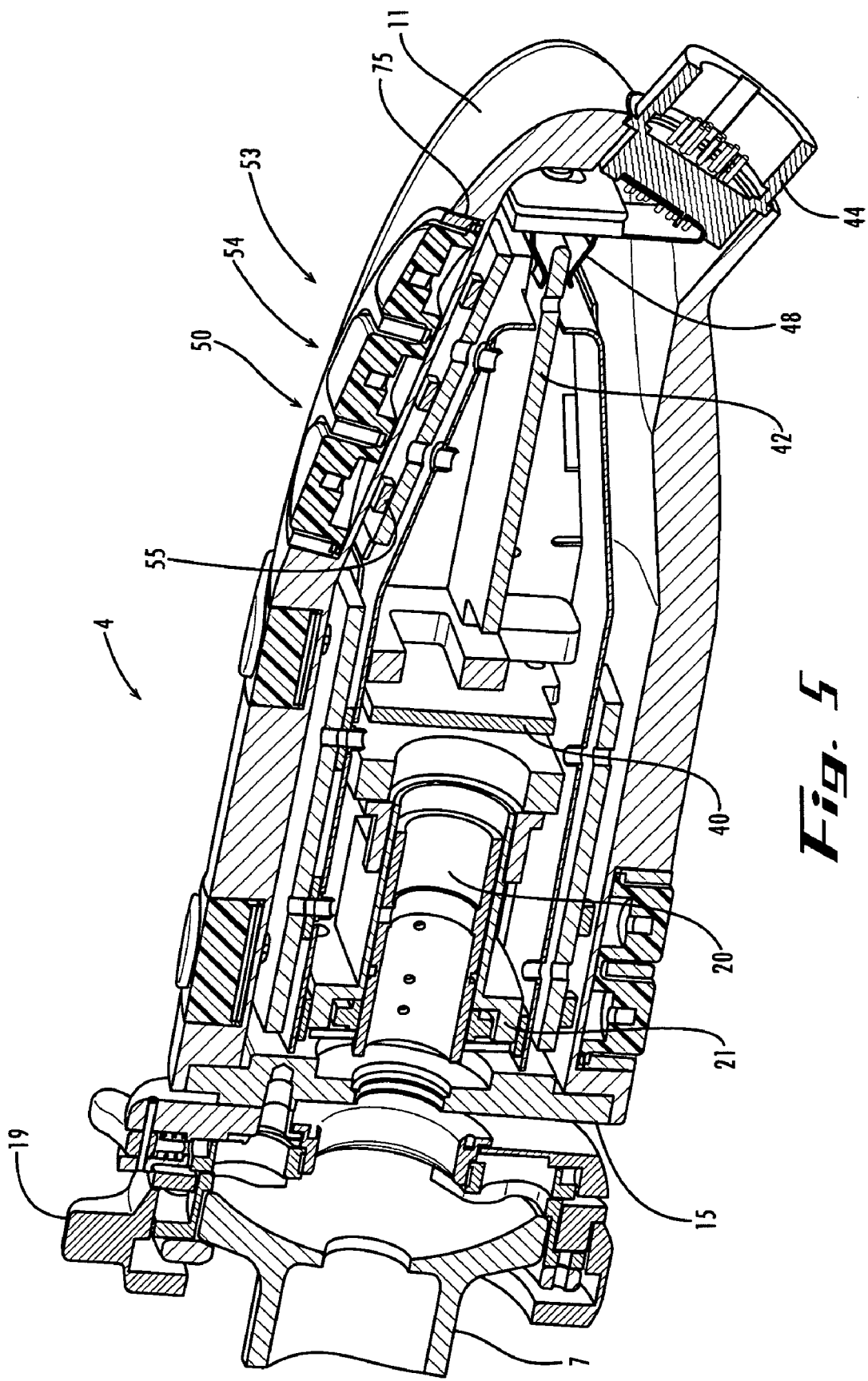
FIG. 5 is a perspective, cross-sectional view of a video camera, in accordance with an embodiment of the present invention.

Referring also to FIG. 5, one or more keypad sockets 75 are provided in the housing 11 to accept the keypad 53, including an outer bezel 71. The keypad 53 comprises one or more switch sensors 55 mounted within the housing 11. The keypad 53 further comprises a flexible membrane 69 adapted to provide an attachment for one or more sensor targets 60 disposed in cooperative alignment with the switch sensors 55. The keypad 53 further comprises an outer bezel 71 adapted to be disposed over portions of the flexible membrane 69 and in cooperative engagement with the keypad socket 75, in sealing engagement therewith, and coupled to the housing 11 using techniques such as, but not limited to, friction fit, soldering and welding. The outer bezel 71 comprises one or more outer bezel apertures 72 associated with each of the sensor targets 60 that define the portions of the flexible membrane 69 for engagement by the operator.

Figure 9:
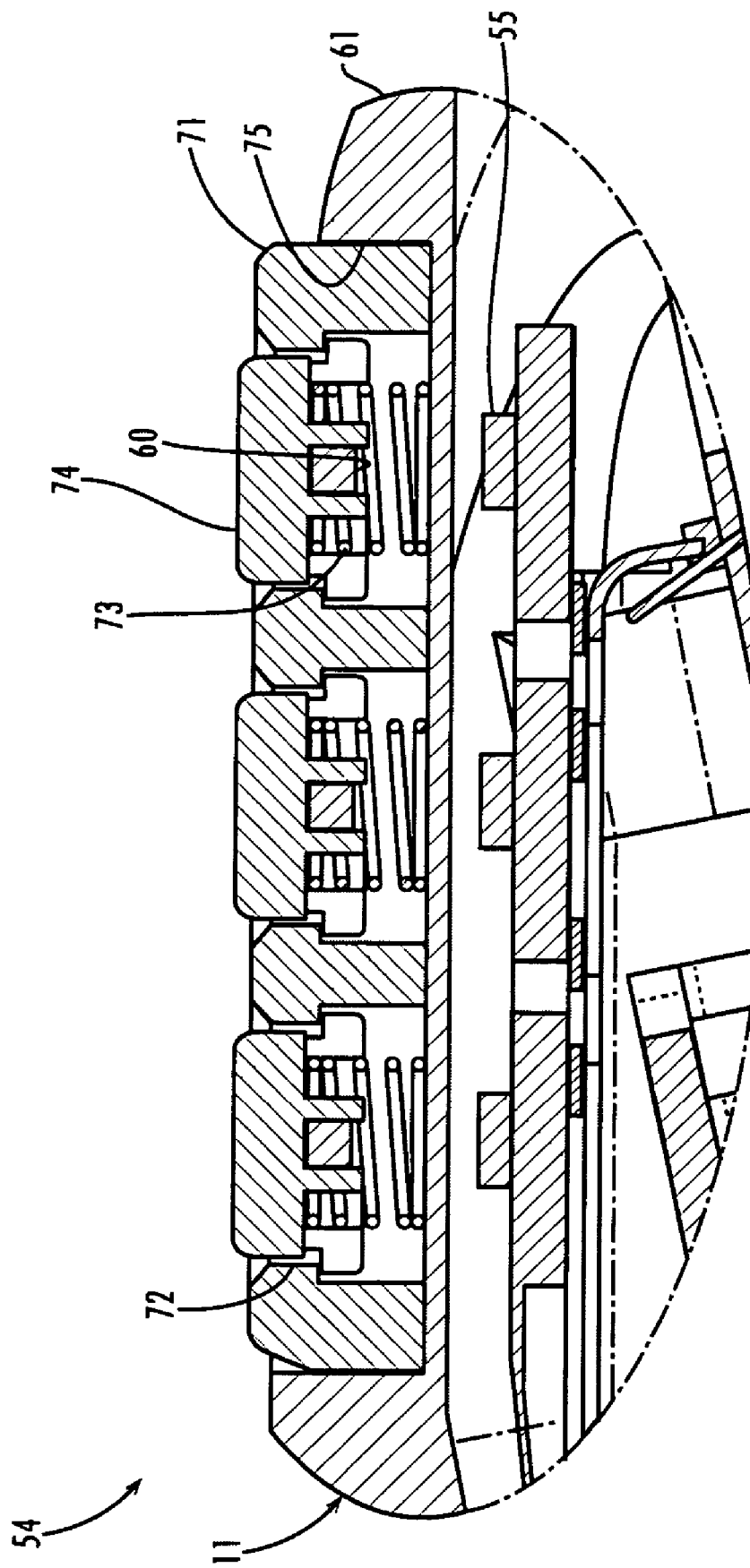
FIG. 9 is a cross-sectional view of a keypad, in accordance with another embodiment of the present invention.

FIG. 9 is a cross-sectional view of a keypad 54 which maintains a hermetic seal with the housing 11, in accordance with another embodiment of the present invention. Switching is accomplished by a finger touch/push of a sensor target 60, with the switch sensor 55 sensing the sensor target 60 by various means across the hermetic barrier 61. The hermetic barrier 61 is an integral part of the housing 11, such as, but not limited to, a recessed portion, defining a keypad socket 75, in the housing 11, wherein the housing 11 comprises a material that allows communication between the sensor target 60 external to the housing 11 and the switch sensor 55 that is internal to the housing 11. In other embodiments in accordance with the present invention, the hermetic barrier 61 can be in the form of a membrane, plate, thin wall, glass, or other material suitable for a particular purpose, hermetically sealed with the housing 11.

One or more keypad sockets 75 are provided in the housing 11 to accept the keypad 54, including an outer bezel 71. The keypad 54 comprises one or more switch sensors 55 mounted within the housing 11. The keypad 54 further comprises a hermetic barrier 61 adapted to retain/maintain a hermetic seal with the housing 11. The keypad 54 further comprises one or more buttons 74 adapted to provide an attachment for one or more sensor targets 60 disposed in cooperative alignment with the switch sensors 55. The keypad 53 further comprises an outer bezel 71 having one or more outer bezel apertures 72 adapted to retain the buttons 74 and maintain alignment of the sensor targets 60 with switch sensors 55. The keypad 54 further comprises biasing members 73, such as, but not limited to, a helical spring, adapted to bias the button 74 in an up-position away from the switch sensor 55 while allowing the button 74 to be depressed moving the sensor target 60 closer to the switch sensor 55. The outer bezel 71 cooperatively engages with the keypad socket 75, in sealing engagement therewith, and coupled to the housing 11 using techniques such as, but not limited to, friction fit, soldering and welding.

The following discussion defines various sensors, barriers, targets and mode of operation for each.

In accordance with an embodiment of the present invention, the switch sensor is an optical reflective sensor-switch which responds to an optical input. The barrier is a transparent material, such as, but not limited to, glass, sapphire and clear plastic. The sensor target is a reflective material, such as, but not limited to, a mirror and polished metal. Finger pressure on the flexible membrane changes the position of the sensor target which results in a change in the optical coupling between the sensor target and the switch sensor. The switch sensor responds to the change in optical coupling by closing or opening an electrical connection.

In accordance with another embodiment of the present invention, the switch sensor is a magnetic-flux responsive switch, such as, but not limited to, a reed switch and a Hall-effect switch, which responds to a change in magnetic flux. The barrier is a non-magnetic material, such as, but not limited to, aluminum, titanium, magnesium, 300 series stainless steel, glass, sapphire and plastic. The sensor target is a magnet. Finger pressure on the flexible membrane 69 changes the position of the magnet which results in a change in the magnetic flux on the switch sensor. The switch sensor responds to the change in magnetic flux by closing or opening an electrical connection.

In accordance with another embodiment of the present invention, the switch sensor is a capacitive sensor circuit which responds to a change of capacitance. The barrier is a polymeric material that is non-conductive. The sensor target is an electrically-conductive metal or direct finger contact. Finger contact changes the capacitance at the capacitive sensor circuit. The capacitive sensor circuit responds to the change in capacitance by closing or opening an electrical connection.

In accordance with another embodiment of the present invention, the switch sensor is a pressure sensitive sensor, such as, but not limited to, a strain gage and a dome switch, which responds to finger pressure. The barrier is a thin sheet metal or polymer adapted to flex under finger pressure. The target is a button or direct finger contact. Finger pressure deforms the thin sheet to allow pressure onto the pressure sensitive sensor. The switch sensor responds to the change in pressure by closing or opening an electrical connection.

In some embodiments, the flexible membrane is hard-coated with parylene, or other material such as silicone, polyester, so that moisture won't be able to get through. Also, the flexible membrane is so constructed that it, when compressed between the housing 11 and outer bezel 71 during assembly, a seal is created to seal against moisture from reaching space between flexible membrane 69 and the hermetic seal barrier 68 and/or housing 11. The outer bezel 71 is coupled using techniques such as, but not limited to, soldering and welding, to make a hermetic seal with the housing 11 so moisture won't be able to get through via the bezel-housing seam.

Referring again to FIG. 1, the video camera endoscopic system 2 combines the motorized video camera 4 similar to the embodiments described above with an endoscope 6. The coupler 19 is adapted to be releasably coupled to the conventional endoscope 6. In the embodiment of FIG. 1, the coupler 19 is provided with a bayonet type lock, for attaching it to an endoscope 6. In an embodiment, the coupler 19 is threaded for making a screw connection to the proximal end of the endoscope 6.

With a video camera endoscopic system 2 as illustrated in FIGS. 1-7, a surgeon is able to precisely focus the image captured by an endoscope onto the image focal plane of the video camera over a relatively wide range of object distances, characterized by substantial changes in magnification and fields of view. Focusing the video camera is straightforward. If the captured image displayed by the display device is not in focus or if the surgeon wishes to change magnification and fields of view by increasing or decreasing the object distance, the surgeon activates and controls the operation of motor 32 so as to cause its output shaft to rotate in the "forward" or "reverse" drive mode, as required, to cause the lens cell to move in a direction that will bring the displayed image into sharp focus. The amount and speed of movement of the lens cell will depend upon the motor speed and the gearing. The gearing parameters are predetermined to permit the lens cell to be moved precisely in small increments so as to facilitate sharp focusing.

It is within the contemplation of the present invention that any well known apparatus for operating a reversible motor may be used in association with the present invention. It also is contemplated that the apparatus may be combined with an autofocus system (not shown) which is capable of automatically maintaining the image viewed by the surgeon in sharp focus. For example, autofocus systems are known which electrically sample the output image quality and provide control signals which operate a motor drive, so as to adjust the position of a focusing lens unit in a direction to ensure the presentation of the sharpest image possible with the available optical system. Other autofocus systems which measure object distance may be used to control operation of the focusing device. Embodiments of the present invention that incorporate autofocus systems may not require the need for the keypad switches provided above.

Embodiments of the video camera described above have numerous advantages. The video camera is hermetically sealed and autoclave sterilizable, easily, repeatedly and efficiently. Also, the lens cell and the motor drive system can be optically and mechanically aligned and tested prior to assembly in the housing. Further, the video camera retains the ability to remove the lens cell and the motor drive system for repair or replacement. A further advantage is that the lens cell is driven by an internal electromechanical drive system, and hence free of hard to clean and sterilize features that are typical of manual focusing devices.

Although specific forms of an endoscope video camera and a system utilizing the same have been described and illustrated herein, it is to be understood that such have been disclosed by way of illustration, rather than by way of limitation. Those skilled in the art will realize from the foregoing specification that a video camera wherein the lens cell is internally electromechanically movable in a housing may be applied in numerous other optical contexts. Thus, for example, the video camera described might be coupled to an optical image capturing device other than an endoscope. It is intended that the present invention be understood as being limited only by the terms of the appended claims.

What is claimed:

1. An electronic video camera for an endoscope, comprising:
    an enclosure having a housing and a cover, the housing defining a cavity therein, the cover having a window therein, the housing and cover adapted for hermetic coupling;
    a lens cell having at least one lens;
    a lens cell holder, wherein the lens cell is slidably disposed in the lens cell holder;
    an image sensor in optical communication with the lens cell and window;
    a motorized focusing system adapted to axially reciprocally move the lens cell relative to the lens cell holder; and
    switch controls disposed on the enclosure and in electrical communication with the motorized focusing system, the switch controls hermetically sealed with the enclosure, wherein the lens cell, lens cell holder, image sensor, and the motorized focusing system, as an assembly, are coupled to the cover and disposed within the cavity.

2. The video camera of claim 1, wherein the cavity is defined by a single axial bore, wherein the lens cell holder, the lens cell, the image sensor, and the motorized focusing system are adapted to be disposed within the axial bore.

3. The video camera of claim 2, wherein the housing has a housing proximal end that is closed and a housing distal end that is open, the cover having a cover interior side and a cover external side, the cover defining a stepped annular aperture, the window being hermetically sealed within the stepped annular aperture, the window adapted to be optically transparent, the cover exterior side adapted to optically and mechanically couple with an endoscope.

4. The video camera of claim 3, wherein the window comprises a metalized perimeter adapted for hermetically coupling with the stepped annular aperture to create a hermetic seal with the cover.

5. An electronic video camera for an endoscope, comprising:
    an enclosure having a housing and a cover, the housing defining a cavity therein, the cover having a window therein, the housing and cover adapted for hermetic coupling;
    a lens cell having at least one lens;
    a lens cell holder, wherein the lens cell is slidably disposed in the lens cell holder;
    an image sensor in optical communication with the lens cell and window;
    a motorized focusing system adapted to axially reciprocally move the lens cell relative to the lens cell holder;
    switch controls disposed on the enclosure and in electrical communication with the motorized focusing system, the switch controls hermetically sealed with the enclosure, wherein the lens cell, lens cell holder, image sensor, and the motorized focusing system, as an assembly, are coupled to the cover and disposed within the cavity;
    wherein the cavity is defined by a single axial bore, wherein the lens cell holder, the lens cell, the image sensor, and the motorized focusing system are adapted to be disposed within the axial bore;
    wherein the housing has a housing proximal end that is closed and a housing distal end that is open, the cover having a cover interior side and a cover external side, the cover defining a stepped annular aperture, the window being hermetically sealed within the stepped annular aperture, the window adapted to be optically transparent, the cover exterior side adapted to optically and mechanically couple with an endoscope; and
    wherein the housing proximal end comprises a cable connector hermetically coupled with the housing and adapted to allow electrical communication therethrough, and wherein the cavity adjacent to the housing proximal end comprises electronic connectors in electrical communication with the cable connector, the motorized focusing system and the image sensor in electrical communication with the electronic connectors.

6. The video camera of claim 5, wherein the electronic connectors are adapted to electrically couple with complementary connectors associated with the associated electronics of the image sensor and the motorized focusing system.

7. The video camera of claim 5, wherein the lens cell further comprises a key depending therefrom, and the lens cell holder further comprises a keyway, the key is adapted to cooperate with the keyway for the retention of rotational alignment of the lens cell relative to the lens cell holder and to limit the range of linear travel there between.

8. The video camera of claim 1, wherein the motorized focusing system comprises a motor and associated drive components, the motor being coupled to the lens cell holder and adapted to linearly translate the lens cell within the lens cell holder.

9. The video camera of claim 8, wherein the associated drive components comprise:
    a pinion gear having pinion gear teeth;
    a lens cell gear having lens cell gear internal threads and lens cell gear external teeth; and
    wherein the lens cell has an outer surface comprising lens cell external threads, the pinion gear disposed on a motor drive shaft extending from the motor, the lens cell gear disposed over the lens cell with the lens cell gear internal threads in cooperative engagement with the lens cell external threads, the lens cell gear external teeth in cooperative engagement with the pinion gear teeth such that rotation of the pinion gear will cause the lens cell to move longitudinally in the lens cell holder and in axial alignment with the optical axis.

10. A keypad for maintaining a hermetic seal with a housing, comprising a means for sensing finger motion and a means for converting that motion to an electric signal transmitted internal to the housing.

11. The keypad of claim 10, comprising:
    a plurality of switch sensors coupled to the housing, the sensors covered with a barrier that is hermetically sealed with the housing.

12. The keypad of claim 11, wherein the switch sensors comprise a multiple dome keypad (MDK) and keypad electrical connectors, the MDK comprises a plurality of flexible membrane elements that are pressure sensitive and respond to finger pressure to close an electrical switch, the MDK is coupled on the housing and hermetically sealed therewith with a flexible membrane barrier, the flexible membrane barrier adapted to allow finger pressure to deform the flexible membrane barrier so as to allow contact with snap buttons, the electrical connectors are adapted to be coupled to associated electronics controlling the motorized focusing system and image sensor.

* * * * *

UNITED STATES PATENT AND TRADEMARK OFFICE
CERTIFICATE OF CORRECTION

| | | |
|---|---|---|
| PATENT NO. | : 7,852,371 B2 | Page 1 of 1 |
| APPLICATION NO. | : 11/109902 | |
| DATED | : December 14, 2010 | |
| INVENTOR(S) | : Gregory Konstorum, Tai Lin Fan and Lawrence St. George | |

It is certified that error appears in the above-identified patent and that said Letters Patent is hereby corrected as shown below:

On the Title Page:

Column 1, Item (73), change "Gyrus Acmi, Inc." to --Gyrus ACMI, Inc.--

Signed and Sealed this
Twenty-sixth Day of April, 2011

David J. Kappos
*Director of the United States Patent and Trademark Office*